United States Patent
Frankel et al.

[11] 4,092,336
[45] May 30, 1978

[54] DINITROCYANOALKYL EPOXIDES

[75] Inventors: Milton B. Frankel, Tarzana; Naomi N. Ogimachi, Canoga Park, both of Calif.

[73] Assignee: Rockwell International Corporation, El Segundo, Calif.

[21] Appl. No.: 630,489

[22] Filed: Apr. 5, 1967

[51] Int. Cl.² .................................. C07D 303/08
[52] U.S. Cl. .................................. 260/348.45; 149/88; 260/465.1
[58] Field of Search ................ 260/348 R, 465.1, 644, 260/348.45; 149/88

[56] References Cited

U.S. PATENT DOCUMENTS

| 3,316,278 | 4/1967 | Linden et al. | 260/348.45 |
| 3,335,155 | 8/1967 | Linden et al. | 260/348.45 |

Primary Examiner—Leland A. Sebastian
Attorney, Agent, or Firm—L. Lee Humphries; Robert M. Sperry

[57] ABSTRACT

Dinitrocyanoalkyl epoxides having the general formula:

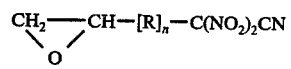

wherein R is a lower alkylene radical containing from 1 through 5 carbon atoms and $n$ is 0 or 1.

4 Claims, No Drawings

DINITROCYANOALKYL EPOXIDES

BACKGROUND OF THE INVENTION

There exists a need for energetic binders that are thermally stable and that are not highly impact sensitive. This need is most urgently felt in the area of tactical ordnance. These binders are most suitably provided in the form of polymers, for ease of manufacture. There exists a corresponding need for monomers capable of producing such energetic polymers suitable for the uses described.

It is an object of this invention to provide a new class of chemical compounds.

It is a further object of this invention to provide a new class of monomers.

It is a still further object of this invention to provide a new class of monomers suitable for polymerization into polymers useful as energetic binders.

SUMMARY OF THE INVENTION

The novel compounds of the instant invention are dinitrocyanoalkyl epoxides having the general formula:

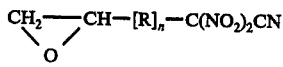

wherein R is an alkylene radical of from 1 through 5 carbon atoms and $n$ is 0 or one.

The compounds of this invention are prepared by the epoxidation of dinitrocyanomethyl olefins with peroxytrifluoroacetic acid, in accordance with the general reaction scheme set forth below:

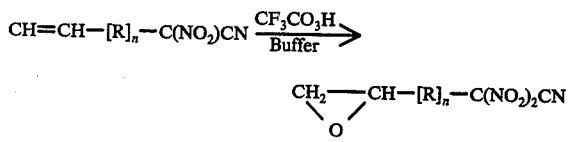

wherein R and $n$ are as defined above. The reaction should be buffered to a pH of between 6 and 11. The dinitrocyanomethyl olefins may be prepared according to the procedure as set forth by Hammond, et al., Tetrahedron, Vol. 19, Supplement 1, pp. 177–195, 1963.

For reasons of safety, it is preferred that the reaction be carried out in solution. This preferred synthesis is carried out by preparing a methylene chloride solution of peroxytrifluoroacetic acid, generated in situ from 90% hydrogen peroxide and trifluoroacetic anhydride. This solution is then added to a boiling mixture of the olefin in methylene chloride with disodium hydrogen phosphate as the buffer. Methylene chloride is convenient for the reflux reaction due to its low boiling point. Naturally, other chlorinated solvents such as chloroform, trichlorethylene, and chlorobenzene would be suitable. Moreover, other solvents not reactive with the reactants can be used. The use of peroxytrifluoroacetic acid in a buffed medium for the epoxidation of negatively substituted olefins has been described. [W. D. Emmons and A. S. Pagano, J. Am. Chem. Soc., 77, 98 (1955).]

DESCRIPTION OF THE PREFERRED EMBODIMENTS

To more clearly illustrate this invention, the following example is presented.

EXAMPLE I

Preparation of 1,1-dinitro-1-cyano-3,4-epoxybutane

A solution of peroxytrifluoracetic acid was prepared from 1.70 ml, 0.062 moles, of 90% hydrogen peroxide, 10.5 ml, 0.074 moles, of trifluoroacetic anhydride, and 12 ml of methylene chloride. This reagent was added over a 35 minute period to a well stirred, boiling mixture of 8.2 g, 0.048 moles, of 1,1-dinitro-1-cyano-3-butene, 50 ml of methylene chloride, and 27.5 g, 0.192 moles, of disodium hydrogen phosphate. After this mild exothermic reaction had subsided, the solution was heated under reflux for 2½ hours. The resulting mixture was stirred with 75 ml of water until all the inorganic salts had dissolved. The organic layer was separated and the aqueous layer was extracted with 2–10 ml portions of methylene chloride. The combined methylene chloride extracts were washed with 15 ml of 10% sodium bicarbonate solution and dried over magnesium sulfate. The solvent was removed at reduced pressure and the residual liquid was fractionated through a small Vigreux column to yield 3.6 g of unreacted 1,1-dinitro-1-cyano-3-butene and 3.17 g (63% yield) of 1,1-dinitro-1-cyano-3,4-epoxybutane, b.p. 62°–64°/0.005 mm., $N^{25}D$ 1.4672. The infrared spectrum was consistent with the assigned structure.

Anal. Calc'd for $C_5H_5N_3O_5$: C, 32.09; H, 2.67; N, 22.46; epoxy oxygen, 8.57; Found : C, 32.01; H, 2.65; N, 22.63; epoxy oxygen, 8.37.

A wide variety of compounds can be prepared in accordance with the example set forth above. 1,1-dinitro-1-cyano-2,3-epoxpropane is prepared by the epoxidation of 1,1-dinitro-1-cyano-2-propene, 1,1-dinitro-1-cyano-4,5-epoxpentane is prepared from 1,1-dinitro-1-cyano-4-pentene, 1,1-dinitro-1-cyano-5,6-epoxyhexane is prepared from 1,1-dinitro-1-cyano-5-hexene, 1,1-dinitro-1-cyano-6,7-epoxyheptane is prepared from 1,1-dinitro-1-cyano-6-heptene, and 1,1-dinitro-1-cyano-7,8-epoxyoctane is prepared by the epoxidation of 1,1-dinitro-1-cyano-7-octene.

It is apparent from the above discussion that any member of the above series of dinitrocyanoalkyl epoxides can be prepared by the epoxidation of the dinitrocyanomethyl olefin, according to the teachings of this invention.

These dinitrocyanoalkyl epoxides can readily be converted to dihydroxy-terminated liquid prepolymers of varying molecular weight by catalitic reaction, using a catalyst such as $BF_3$ and an initiator containing OH groups, such as water, a glycol, or glycerine. The reaction can be summarized:

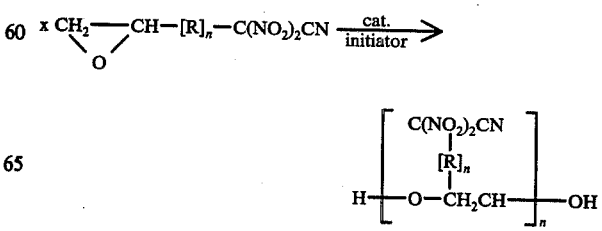

where $x$ is preferably about 10. These liquid prepolymers can be loaded with high percentages of oxidizers and fuel, cast, and cured into a tough resilient composite propellant or explosive composition, which are very energetic.

It is to be understood that the examples presented are merely a means of illustration and are not intended to limit the scope of the invention in any way, the scope of which is defined by the following claims.

We claim:

1. As compositions of matter, dinitrocyanoalkyl epoxides having the formula:

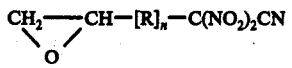

wherein R is a lower alkylene radical of from 1 to 5, and $n$ is 0 or one.

2. The compound of claim 1 where $n$ is 0.

3. The compound of claim 1 where R is methylene and $n$ is one.

4. The compound of claim 1 where R is propylene and $n$ is one.